United States Patent [19]
Narandja et al.

[11] Patent Number: 5,922,684
[45] Date of Patent: Jul. 13, 1999

[54] POLYHYDRO DERIVATIVES OF TYLOSINE AND PROCESS FOR THEIR PREPARATION

[75] Inventors: Amalija Narandja; Nevenka Lopotar, both of Zagreb, Croatia

[73] Assignee: Pliva, Farmaceutska, Kemijska, Prehrambenai Kozmeticka Industrija, Dionicko Drustvo, Zagreb, Croatia

[21] Appl. No.: 08/959,306

[22] Filed: Oct. 28, 1997

[30] Foreign Application Priority Data

Oct. 30, 1996 [HR] Croatia .................................. P960509

[51] Int. Cl.$^6$ ...................................................... A61K 71/31
[52] U.S. Cl. .............................. 514/30; 536/7.1; 536/7.2; 536/7.4
[58] Field of Search ................................. 514/30; 536/7.1, 536/7.2, 7.4

[56] References Cited

U.S. PATENT DOCUMENTS 4,680,386  7/1987  Morimoto et al. ........................ 536/7.2
5,023,240  6/1991  Narandja et al. ......................... 514/30

*Primary Examiner*—Frederick Krass
*Attorney, Agent, or Firm*—Pollock, Vande Sande & Amernick

[57] ABSTRACT

The invention relates to 13-hydroxy-tylosine derivatives, novel semisynthetic antibiotics from the class of macrolides, and to a process for the preparation thereof. According to the present invention by a reductive opening of the oxirane ring of tylosine 13-hydroxy compounds are obtained, which are then subjected to a hydrogenation of the double bond and then 13-hydroxy dihydro or tetrahydro compounds are subjected to an oximation reaction or 13-hydroxy oximes are subjected to the hydrogenation of the double bond.

26 Claims, No Drawings

POLYHYDRO DERIVATIVES OF TYLOSINE AND PROCESS FOR THEIR PREPARATION

TECHNICAL FIELD OF THE INVENTION

IPC

A 61 K 31/70

C 07 H 17/8

1. Technical Problem

The present invention relates to tylosine derivatives, novel synthetic products from the class of 16-membered macrolides with antimicrobial activity. More precisely, the invention relates to 13-hydroxy dihydro and tetrahydro tylosine derivatives of the formula I

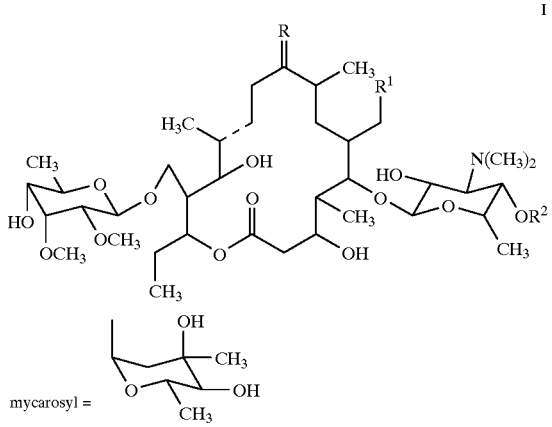

wherein R stands for O or NOH, $R^1$ stands for CHO, $CH(OCH_3)_2$ or CH=NOH; $R^2$ stands for mycarosyl or H and the line—stands for a double or a single bond, as well as to a process for the preparation of said compounds.

2. Prior Art

It is well known that 12,13-epoxy compounds were prepared by oxidation of tylosine derivatives (A. K. Mallams, U.S. Pat. No. 4,808,575).

It is known that by catalytical hydrogenation of 12,13-epoxy tylosine, 10,11-dihydro-12,13-epoxy compounds were obtained (A. Narandja, HR appln. P 950449A).

It is also known that C-9 and C-20 oximes of tylosine derivatives and of 10,11,12,13-tetrahydro-tylosine derivatives were prepared (A. Narandja, U.S. Pat. No. 5,023,240).

In view of the known prior art, reductive opening of the oxirane ring of 12,13-epoxy derivatives of tylosine, isomerization and preparation of 13-hydroxy dihydro and tetrahydro derivatives of tylosine have not yet been described.

DESCRIPTION OF TECHNICAL PROBLEM WITH EXAMPLES

It has been found that derivatives of 13-hydroxy-tylosine of the formula I wherein R stands for O or NOH, $R^1$ stands for CHO, $CH(OCH_3)_2$ or CH=NOH; $R^2$ stands for mycarosyl or H and the line—stands for a double or a single bond, can be prepared in such a manner that a compound of the formula II wherein R stands for CHO or $CH(OCH_3)_2$ and $R^1$ stands for mycarosyl or H, is subjected to reduction with Zn powder in a mixture of a lower $(C_1-C_3)$-alcohol and water under the addition of 3–5% w/v of ammonium chloride at a pH value of 2–7, preferably within a range of 5.0–5.5, at room temperature for 3–6 hours and, subsequently, the obtained compound of the formula I, wherein R stands for O, $R^1$ stands for CHO or $CH(OCH_3)_2$, $R^2$ stands for mycarosyl or H and the line—stands for a double bond, is optionally subjected to an oximation reaction with 1–8 equivalents of hydroxylamine hydrochloride in pyridine or a lower alcohol under the addition of a base (pyridine or $Na_2CO_3$) in nitrogen stream, at room temperature or reflux temperature for 3–10 hours; or, optionally, a compound of the formula I, wherein R stands for O or NOH, $R^1$ stands for $CH(OCH_3)_2$, $R^2$ stands for mycarosyl or H and the line—stands for a double bond, is subjected to a hydrogenation reaction in an organic solvent, preferably a lower $(C_1-C_3)$-alcohol, in the presence of 3–6% w/w of palladium-on-charcoal at a hydrogen pressure of 0.2–0.5 MPa at room temperature for 6–12 hours, or optionally, a compound of the formula I, wherein R stands for O, $R^1$ stands for CHO or $CH(OCH_3)_2$, $R^2$ stands for mycarosyl or H and the line—stands for a single bond, is subjected to an oximation reaction in the above described manner.

According to the present invention, novel compounds are isolated from aqueous alkaline solutions by conventional extraction methods with halogenated hydrocarbons such as methylene chloride, chloroform or carbon tetrachloride and by evaporation to a dry residue.

The course of reaction is followed by thin-layer chromatography (Silicagel 60 $F_{254}$, Merck) in the solvent system methylene chloride-methanol-ammonium hydroxide 25% (90:9:1.5, system E; 90:9:0.5, system E1) or ethylacetate-methanol-ammonium hydroxyde 25% (85:10:5, system C). Optionally, the separation of the reaction products or the purification of the products for the purpose of spectral analyses are carried out on a silicagel column (Silicagel 60, Merck Co., 230–400 mesh/ASTH or 60–230 mesh/ASTH) in solvent systems E or E1. The identification of the novel compounds is carried out by UV and NMR spectroscopy.

Novel compounds exhibit antibacterial action, but they can also be used as intermediates for the preparation of novel tylosine derivatives.

The invention is illustrated by the following examples, which, however, do not in any way limit the scope of the invention.

EXAMPLE 1

13-Hydroxy-10,13-dihydro-desmycosin 20-dimethylacetal (1)

12,13-Epoxy-desmycosin-20-dimethylacetal (10 g, 12.0 mmoles) was dissolved in ethanol (200 ml), whereupon $NH_4Cl$ (31 g) dissolved in water (400 ml) and gradually Zn powder (31 g) were added. It was stirred at room temperature for 5 hours, whereat the pH value was kept at 5–5.5. After completing of the reaction, Zn was separated by filtration, the reaction solution was evaporated at a reduced pressure to half of its volume, by adding 10% NaOH the pH was adjusted to 8.5 and it was extracted with chloroform (2×100 ml). The combined extracts were dried and evaporated to a dry residue. The crude product was purified on a silicagel column in the solvent system E.

Obtained: 5.2 g (52%), Rf(E) 0.45, Rf(C) 0.41.

$^1$H-NMR ($CDCl_3$) ppm: 5.78 (1H, d, H-11), 4.58 (1H, d, 1'''), 4.56 (1H, t, H-20), 4.24 (1H, d, 1'), 3.64 (3H, s, 3'''OMe), 3.51 (3H, s, 2'''OMe), 2.52 (6H, s, $NMe_2$), 1.68 (3H, s, 12-Me).

$^{13}$C-NMR ($CDCl_3$) ppm: 211.4 (s, C-9), 173.1 (s, C-1), 139.7 (s, C-12), 117.3 (d, C-11), 103.6 (d, C-1'), 102.0 (d, C-20), 101.3 (d, C-1'''), 76.5 (d, C-13), 12,5 (q, C-22).

EXAMPLE 2

13-Hydroxy-10,13-dihydro-tylosine 20-dimethylacetal (2)

12,13-Epoxy-tylosine-20-dimethylacetal (10 g, 10.2 mmoles) was dissolved in ethanol (200 ml), whereupon $NH_4Cl$ (33 g) dissolved in water (400 ml) and gradually Zn powder (30 g) were added. It was stirred at room temperature for 6 hours and isolated as described in the Example 1.

Obtained: 5.0 g (50%), Rf(E) 0.55, Rf(C) 0.51.

$^1$H-NMR ($CDCl_3$) ppm: 5.79 (1H, d, H-11), 5.09 (1H, d, 1''), 4.59 (1H, d, 1'''), 4.58 (1H, t, H-20), 4.24 (1H, d, 1'), 3.64 (3H, s, 3'''OMe), 3.51 (3H, s, 2'''OMe), 2.51 (6H, s, $NMe_2$), 1.69 (3H, s, 12-Me).

$^{13}$C-NMR ($CDCl_3$) ppm: 211.5 (s, C-9), 172.9 (s, C-1), 139.9 (s, C-12), 117.4 (d, C-11), 103.7 (d, C-1'), 102.1 (d, C-20), 101.5 (d, C-1'''), 98.7 (d, C-1''), 76.6 (d, C-13), 12.6 (q, C-22).

EXAMPLE 3

13-Hydroxy-10,13-dihydro-desmycosin (3)

Process A

Compound 1 (5 g, 6 mmoles) was dissolved in acetonitrile (50 ml) and 1% aqueous trifluoroacetic acid solution (50 ml) and it was stirred at room temperature for 2 hours. The reaction solution was alkalized to pH 8.5 by adding 10% NaOH and extracted with chloroform (2×60 ml). The combined extracts were washed with a saturated $NaHCO_3$ solution and evaporated to a dry residue. By chromatography on a silicagel column in the solvent system E there were obtained 1.65 g (35%) of the product, Rf(E) 0.32.

$^1$H-NMR ($CDCl_3$) ppm: 9.61 (1H, s, H-20), 5.77 (1H, d, H-11), 4.57 (1H, d, 1'''), 4.23 (1H, d, 1'), 3.64 (3H, s, 3'''OMe), 3.51 (3H, s, 2'''OMe), 2.52 (6H, s, $NMe_2$), 1.69 (3H, s, 12-Me).

$^{13}$C-NMR ($CDCl_3$) ppm: 211.6 (s, C-9), 203.5 (d, C-20), 173.2 (s, C-1), 139.7 (s, C-12), 117.4 (d, C-11), 103.5 (d, C-1'), 101.3 (d, C-1'''), 76.7 (d, C-13), 12.6 (q, C-22).

Process B 12,13-Epoxy-desmycosin (3 g, 3.8 mmoles) was dissolved in ethanol (50 ml), whereupon $NH_4Cl$ (10 g) and water (100 ml) and gradually Zn powder (10 g) were added. After 6 hours the product was isolated as described in Example 1. There were obtained 1.8 g (60%) of the product with spectral characteristics as in Example 3A.

EXAMPLE 4

13-Hydroxy-10,13-dihydro-desmycosin-9(E+Z) oxime 20-dimethylacetal (4, 5)

Process A

Compound 1 (5 g, 6 mmoles) was dissolved in methanol (100 ml), whereupon $Na_2CO_3$ (2.2 g) and hydroxylamine hydrochloride (2.9 g, 43 mmoles) were added and it was stirred in nitrogen stream at reflux temperature for 3 hours. The reaction solution was poured into 200 ml of water and by adding 10% NaOH the pH was adjusted to 9.0. It was extracted with chloroform (2×80 ml), dried and evaporated to a dry residue. The crude product (4.7 g) was purified by chromatography on a silicagel column in the solvent system E.

There were obtained 1.27 g (25%) of the product 4, Rf(E) 0.36 (isomer Z), $^1$H-NMR (DMSO $d_6$) ppm: 10.49 (1H, s, 9-NOH), disappears by shaking with $D_2O$, ($CDCl_3$) ppm: 5.73 (1H, d, H-11), 4.60 (1H, d, 1'''), 4.52 (1H, t, H-20), 4.25 (1H, d, 1'), 4.18 (1H, d, H-13), 3.65 (3H, s, 3'''OMe), 3.53 (3H, s, 2'''OMe), 2.53 (6H, s, $NMe_2$), 1.62 (3H, s, 12-Me).

$^{13}$C-NMR ($CDCl_3$) ppm: 174.2 (s, C-1), 162.0 (s, C-9), 139.1 (s, C-12), 120.9 (d, C-11), 103.6 (d, C-1'), 103.1 (d, C-20), 101.0 (d, C-1'''), 76.9 (d, C-13), 27.5 (d, C-8), 11.8 (q, C-22).

and 2.04 g (40.0%) of the less polar product 5, Rf(E) 0.25, (isomer E).

$^1$H-NMR (DMSO-$d_6$) ppm: 10.35 (1H, s, 9-NOH), disappears by shaking with $D_2O$, 5.25 (1H, d, H-11), 4.43 (1H, d, 1'''), 4.42 (1H, t, H-20), 4.30 (1H, d, 1'), 3.94 (1H, d, H-13), 3.65 (3H, s, 3'''OMe), 3.36 (3H, s, 2'''OMe), 2.41 (6H, s, $NMe_2$), 1.62 (3H, s, 12-Me).

$^{13}$C-NMR ($CDCl_3$) ppm: 171.6 (s, C-1), 162.8 (s, C-9), 138.8 (s, C-12), 121.9 (d, C-11), 103.2 (d, C-1'), 103.0 (d, C-20), 101.2 (d, C-1'''), 75.8 (d, C-13), 35.6 (d, C-8), 11.9 (q, C-22).

Process B

Compound 1 (2.5 g, 3 mmoles) was dissolved in pyridine (12 ml), whereupon hydroxylamine hydrochloride (1.62 g, 24 mmoles) was added and it was stirred in nitrogen stream at room temperature for 10 hours. To the reaction solution water (100 ml) was added, it was alkalized to pH 9 and evaporated to one third of its volume. It was extracted with chloroform at pH 5.5 (20 ml) and pH 9 (2×20 ml). The combined extracts of pH 9 were evaporated to dryness. The crude product was purified on a silicagel column (system E1).

There were obtained 0.7 g (27.5%) of the isomer Z and 1.1 g (43%) of the isomer E with the same spectral characteristics as in the process 4A.

EXAMPLE 5

13-Hydroxy-10,13-desmycosin-20(sin+anti)oxime (6, 7)

Compound 3 (3 g, 3.8 mmoles) was dissolved in ethanol (60 ml), whereupon pyridine (1.5 ml) and hydroxylamine hydrochloride (0.26 g, 3.8 mmoles) were added and it was stirred in nitrogen stream at room temperature for 1 hour. To the reaction solution 50 ml of water were added and the isolation was carried out as described in Example 4B. The crude product (2.4 g) was chromatographed on a silicagel column (system E1).

Obtained: 0.9 g (29.4%) of the product 6, Rf(E) 0.32 (sin isomer), $^1$H-NMR (DMSO-$d_6$) ppm: 10.34 (1H, s, 20-NOH), disapears by shaking with $D_2O$, (CDCl$_3$) ppm: 7.45 (1H, t, H-20), 5.78 (1H, d, H-11), 4.58 (1H, d, 1'''), 4.25 (1H, d, H-13), 4.24 (1H, d, 1'), 3.65 (3H, s, 3'''OMe), 3.52 (3H, s, 2'''OMe), 2.52 (6H, s, NMe$_2$), 1.65 (3H, s, 12-Me).

$^{13}$C-NMR (CDCl$_3$) ppm: 211.8 (s, C-9), 172.9 (s, C-1), 151.3 (d, C-20), 139.9 (s, C-12), 118.0 (d, C-11), 103.5 (d, C-1'), 101.3 (d, C-1'''), 76.5 (d, C-13), 12.3 (q, C-22).

and 0.83 g (27.0%) of the less polar product 7, Rf(E) 0.28 (anti isomer).

$^1$H-NMR (DMSO-$d_6$) ppm: 10,65 (1H, s, NOH), disapears by shaking with $D_2O$, (CDCl$_3$) ppm: 6.77 (1H, t, H-20), 5.79 (1H, d, H-11), 4.53 (1H, d, H-20), 4.57 (1H, d, 1'''), 4.24 (1H, d, 1'), 4.22 (1H, d, H-13), 3.65 (3H, 3'''OMe), 3.51 (3H, s, 2'''OMe), 2.52 (6H, s, NMe$_2$), 1.65 (3H, s, 12-Me).

$^{13}$C-NMR (CDCl$_3$) ppm: 211.4 (s, C-9), 173.5 (s, C-1), 152.0 (d, C-20), 139.9 (s, C-12), 118.2 (d, C-11), 103.5 (d, C-1'), 101.3 (d, C-1'''), 76.6 (d, C-13), 12.3 (q, C-22).

EXAMPLE 6

13-Hydroxy-10,13-dihydro-tylosine-9(E+Z)oxime 20-dimethylacetal (8, 9)

Compound 2 (4 g, 4.08 mmoles) was dissolved in pyridine (20 ml), whereupon hydroxylamine hydrochloride (1.95 g, 29 mmoles) was added and it was stirred at room temperature in nitrogen stream for 10 hours. To the reaction solution water (140 ml) was added and it was worked up as described in Example 4B. The crude product (3.2 g) was purified by chromatography on a silicagel column (system E).

Obtained: 0.88 g (21.7%) of the product 8, Rf(E) 0.51, $^1$H-NMR (DMSO-$d_6$) ppm: 10.45 (1H, s, 9-NOH), disapears by shaking with $D_2O$, (CDCl$_3$) ppm: 5.74 (1H, d, H-11), 5.09 (1H, d, 1''), 4.59 (1H, d, 1'''), 4.53 (1H, t, H-20), 4.24 (1H, d, 1'), 3.65 (3H, s, 3'''OMe), 3.53 (3H, s, 2'''OMe), 2.52 (6H, s, NMe$_2$), 1.65 (3H, s, 12-Me).

$^{13}$C-NMR (CDCl$_3$) ppm: 173.9 (s, C-1), 162.1 (s, C-9), 139.3 (s, C-12), 120.0 (d, C-11), 103.5 (d, C-1'), 103.2 (d, C-20), 101.3 (d, C-1'''), 98.7 (d, C-1''), 76.9 (d, C-1), 27.8 (d, C-8), 12.0 (q, C-22).

and 1.62 g (40%) of the less polar product 9, Rf(E) 0.39.

$^{13}$C-NMR (CDCl$_3$) ppm: 172.0 (s, C-1), 162.7 (s, C-9), 138.9 (s, C-12), 122.0 (d, C-11), 103.5 (d, C-1'), 103.1 (d, C-20), 101.2 (d, C-1'''), 98.8 (d, C-1''), 76.0 (d, C-13), 35.8 (d, C-8), 12.0 (q, C-22).

EXAMPLE 7

13-Hydroxy-10,11,12,13-tetrahydro-desmycosin 20-dimethylacetal (10)

Compound 1 (1.5 g, 1.8 mmoles) was dissolved in ethanol (150 ml), 10% Pd/C (0.75 g) was added and it was hydrogenized at the hydrogen pressure of 0.5 MPa at room temperature for 12 hours. The catalyst was separated by filtration, ethanol was evaporated to a dry residue and the crude product was chromatographed on a silicagel column in the solvent system E1.

Obtained: 1.0 g (67%), Rf(E) 0.45, Rf(C) 0.49.

$^1$H-NMR (CDCl$_3$) ppm: 4.58 (1H, d, 1'''), 4.54 (1H, t, H-20), 4.24 (1H, d, 1'), 3.64 (3H, s, 3'''OMe), 3.51 (3H, s, 2'''OMe), 2.52 (6H, s, NMe$_2$), 0.86 (3H, d, 12-Me).

$^{13}$C-NMR (CDCl$_3$) ppm: 213.4 (s, C-9), 173.2 (s, C-1), 103.5 (d, C-1'), 102.2 (d, C-20), 101.4 (d, C-1'''), 71.2 (d, C-13), 20.55 (d, C-22).

EXAMPLE 8

13-Hydroxy-10,11,12,13-tetrahydro-desmycosin-9 (Z)oxime 20-dimethylacetal (11)

Compound 4 (1 g, 1.18 mmoles) was dissolved in ethanol (50 ml), 10% Pd/C (0.5 g) was added and it was hydrogenized at the hydrogen pressure of 0.5 MPa at room temperature for 8 hours. The treatment as in Example 7 gave 0.45 g (45%) of the product, Rf(E) 0.30.

$^1$H-NMR (DMSO-$d_6$) ppm: 10.31 (1H, s, 9-NOH), disappears by shaking with $D_2O$, (CDCl$_3$) ppm: 4.61 (1H, d, 1'''), 4.52 (1H, t, H-20), 4.25 (1H, d, 1'), 3.65 (3H, s, 3'''OMe), 3.53 (3H, s, 2'''OMe), 2.52 (6H, s, NMe$_2$), 0.89 (3H, d, 12-Me).

$^{13}$C-NMR (CDCl$_3$) ppm: 172.5 (s, C-1), 163.8 (s, C-9), 103.6 (d, C-1'), 102.7 (d, C-20), 101.0 (d, C-1'''), 71.2 (d, C-13), 15.3 (q, C-22).

EXAMPLE 9

13-Hydroxy-10,11,12,13-tetrahydro-desmycosin-9 (E)oxime 20-dimethylacetal (12)

Compound 5 (1 g, 1.18 mmoles) was dissolved in ethanol (50 ml), 10% Pd/C (0.5 g) was added and it was hydrogenized at the hydrogen pressure of 0.5 MPa at room temperature for 8 hours. The treatment as in Example 7 gave 0.39 g (39%) of the product, Rf(E) 0.32.

$^1$H-NMR (DMSO-$d_6$) ppm: 10.14 (1H, s, 9-NOH), disappears by shaking with $D_2O$, (CDCl$_3$) ppm: 4.62 (1H, d, 1'''), 4.52 (1H, t, H-20), 4.26 (1H, d, 1), 3.65 (3H, s, 3'''OMe), 3.52 (3H, s, 2'''OMe), 2.52 (6H, s, NME$_2$), 0.95 (3H, d, 12-Me).

$^{13}$C-NMR (CDCl$_3$) ppm: 173.3 (s, C-1), 165.1 (s, C-9), 103.2 (d, C-1'), 102.5 (d, C-20), 101.2 (d, C-1'''), 71.4 (d, C-13), 15.2 (q, C-22).

EXAMPLE 10

13-Hydroxy-10,11,12,13-tetrahydro-desmycosin-9 (E+Z)oxime 20-dimethylacetal (11,12)

Compound 10 (2 g, 2.39 mmoles) was dissolved in pyridine (10 ml), hydroxylamine hydrochloride (1.36 g, 20 mmoles) was added and it was stirred at room temperature in nitrogen stream for 5 hours. The isolation was carried out as in Example 4B and chromatographed on a silicagel column (system E1). There were obtained 0.3 g (15%) of the isomer E, Rf(E) 0.32, with spectral characteristics identical to those of the compound 12 of Example 9 and 0.9 g (44%) of the isomer Z, Rf(E) 0.30, with the spectral characteristics of the compound 11 of Example 8.

We claim:

1. A process for the preparation of 13-hydroxy dihydro or tetrahydro derivatives of tylosine of the formula I

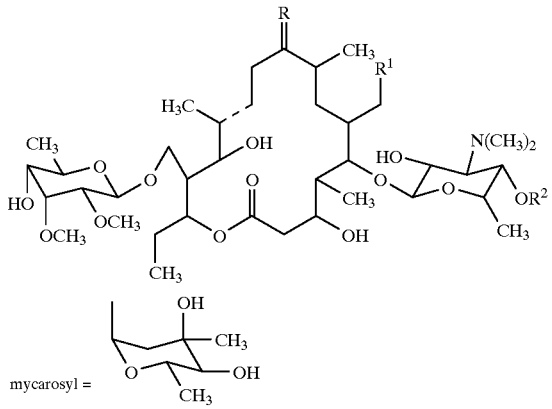

wherein R stands for O or NOH, $R^1$ stands for CHO, $CH(OCH_3)_2$ or CH=NOH; $R^2$ stands for mycarosyl or H and the line—stands for a double or a single bond, characterized in that a compound of the formula II

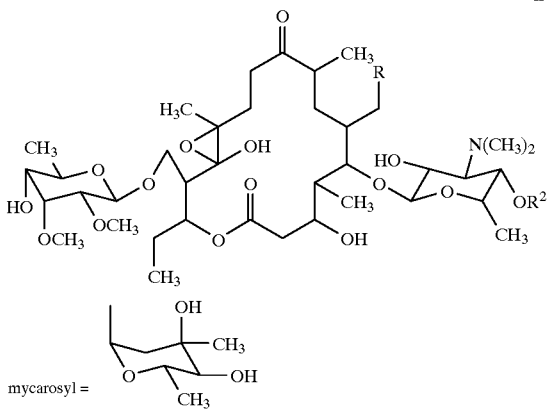

wherein R stands for CHO or $CH(OCH_3)_2$ and $R^1$ stands for mycarosyl or H, is subjected to reduction with Zn powder and then the obtained compound of the formula I, wherein R stands for O, $R^1$ stands for CHO or $CH(OCH_3)_2$, $R^2$ stands for mycarosyl or H and the line—stands for a double bond, is subjected to an oximation reaction; or, the obtained compound of the formula I, wherein R stands for O or NOH, $R^1$ stands for $CH(OCH_3)_2$, $R^2$ stands for mycarosyl or H and the line—stands for a double bond, is subjected to a hydrogenation reaction; or, the obtained compound of the formula I, wherein R stands for O, $R^1$ stands for CHO or $CH(OCH_3)_2$, $R^2$ stands for mycarosyl or H and the line—stands for a single bond, is subjected to an oximation reaction.

2. A process according to claim 1, characterized in that the reduction with Zn powder is carried out in a mixture of a lower $(C_1-C_3)$-alcohol and water under the addition of 3–5% w/v of ammonium chloride at a pH value of 2–7, at room temperature for 3–6 hours.

3. A process according to claim 1, characterized in that the oximation reaction is carried out with 1–8 equivalents of hydroxylamine hydrochloride in pyridine or a lower $(C_1-C_3)$ alcohol under the addition of a base in nitrogen stream, at room temperature or reflux temperature for 3–10 hours.

4. A process according to claim 1, characterized in that hydrogenation is carried out in an organic solvent, under the addition of 3–6% w/w of palladium-on-charcoal at a hydrogen pressure of 0.2–0.5 MPa at room temperature for 6–12 hours.

5. 13-Hydroxy dihydro or tetrahydro derivatives of tylosine of the formula I

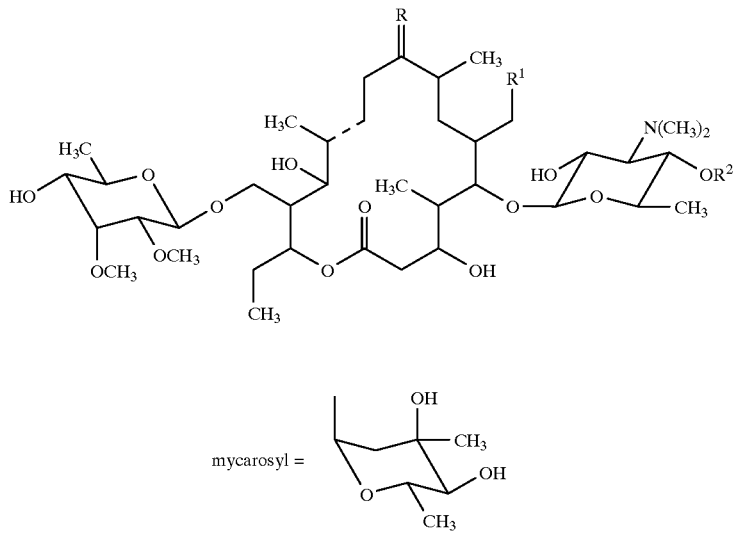

wherein R stands for O, $R^1$ stands for CHO, $CH(OCH_3)_2$ or CH=NOH; $R^2$ stands for mycarosyl or H, and the line—has the meaning of a double or single bond; or wherein R stands for NOH, $R_1$ stands for CHO, CH=NOH or $CH(OCH_3)_2$; $R^2$ stands for mycarosyl or H, and the line—has the meaning of a double or single bond.

6. The derivatives of tylosine according to claim 5 being 13-Hydroxy-10,13-dihydro-tylosine 20-dimethylacetal.

7. The derivatives of tylosine according to claim 5 being 13-Hydroxy-10,13-dihydro-desmycosin 20-dimethylacetal.

8. The derivatives of tylosine according to claim 5 being 13-Hydroxy-10,13-dihydro-tylosine.

9. The derivatives of tylosine according to claim 5 being 13-Hydroxy-10,13-dihydro-desmycosin.

10. The derivatives of tylosine according to claim 5 being 13-Hydroxy-10,13-dihydro-desmycosin-9(E)oxime 20-dimethylacetal.

11. The derivatives of tylosine according to claim 5 being 13-Hydroxy-10,13-dihydro-desmycosin-9(Z)oxime 20-dimethylacetal.

12. The derivatives of tylosine according to claim 5 being 13-Hydroxy-10,13-dihydro-tylosine-9(E)oxime 20-dimethylacetal.

13. The derivatives of tylosine according to claim 5 being 13-Hydroxy-10,13-dihydro-tylosine-9(Z)oxime 20-dimethylacetal.

14. The derivatives of tylosine according to claim 5 being 13-Hydroxy-10,13-dihydro-desmycosin-20(sin)oxime.

15. The derivatives of tylosine according to claim 5 being 13-Hydroxy-10,13-dihydro-desmycosin-20(anti)oxime.

16. The derivatives of tylosine accordinig to claim 5 being 13-Hydroxy-10,11,12,13-tetrahydro-desmycosin 20-dimethylacetal.

17. The derivatives of tylosine according to claim 5 being 13-Hydroxy-10,11,12,13-tetrahydro-tylosine 20-dimethylacetal.

18. The derivatives of tylosine according to claim 5 being 13-Hydroxy-10,11,12,13-tetrahydro-desmycosin.

19. The derivatives of tylosine according to claim 5 being 13-Hydroxy-10,11,12,13-tetrahydro-tylosine.

20. The derivatives of tylosine according to claim 5 being 13-Hydroxy-10,11,12,13-tetrahydro-desmycosin-9-(E)oxime 20-dimethylacetal.

21. The derivatives of tylosine according to claim 5 being 13-Hydroxy-10,11,12,13-tetrahydro-desmycosin-9-(Z)oxime 20-dimethylacetal.

22. The derivatives of tylosine according to claim 5 being 13-Hydroxy-10,11,12,13-tetrahydro-tylosine-9-(E)oxime 20-dimethylacetal.

23. The derivatives of tylosine according to claim 5 being 13-Hydroxy-10,11,12,13-tetrahydro-tylosine-9-(Z)oxime 20-dimethylacetal.

24. The process according to claim 2 wherein the pH is 5.0–5.5.

25. The process according to claim 3 wherein the base is pyridine or $Na_2CO_3$.

26. The process according to claim 4 wherein the organic solvent is a lower ($C_1$–$C_3$) alcohol.

* * * * *

UNITED STATES PATENT AND TRADEMARK OFFICE
CERTIFICATE OF CORRECTION

PATENT NO.　：　5,922,684
DATED　　　：　July 13, 1999
INVENTOR(S)：　Narandja et al

It is certified that error appears in the above-identified patent and that said Letters Patent is hereby corrected as shown below:

Title page, item [73] Assignee, should read ---PLIVA, Farmaceutska, Kemijska, Prehrambena i Kozmeticka Industrija, Dionicko Drustvo, Zagreb, Croatia---

Signed and Sealed this

Twenty-third Day of November, 1999

Attest:

Q. TODD DICKINSON

*Attesting Officer*　　*Acting Commissioner of Patents and Trademarks*

UNITED STATES PATENT AND TRADEMARK OFFICE
CERTIFICATE OF CORRECTION

PATENT NO.   : 5,922,684
DATED        : July 13, 1999
INVENTOR(S)  : Amalija Narandja et al.

It is certified that error appears in the above-identified patent and that said Letters Patent is hereby corrected as shown below:

Columns 2 and 8,
Formula II should read as follows:

--

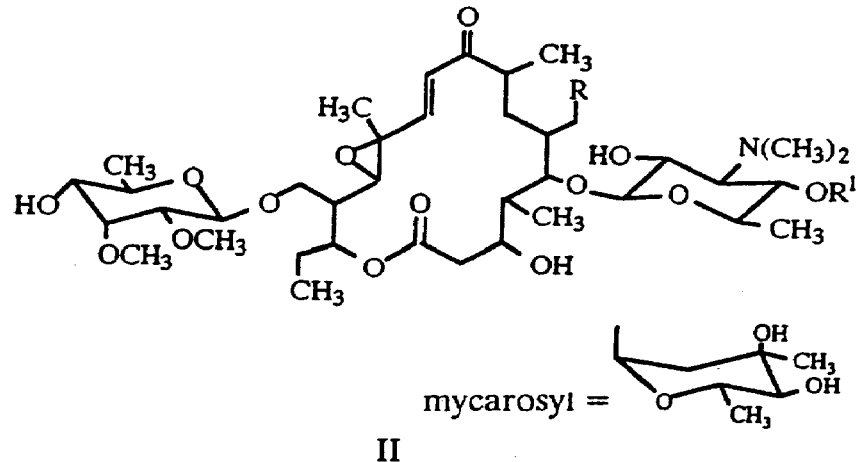

--

Signed and Sealed this

Eighteenth Day of June, 2002

*Attest:*

*Attesting Officer*

JAMES E. ROGAN
*Director of the United States Patent and Trademark Office*